US00PP10448P

United States Patent [19]

Pieters et al.

[11] Patent Number: Plant 10,448

[45] Date of Patent: Jun. 9, 1998

[54] VRIESEA PLANT NAMED CONDOR

[75] Inventors: Luc Pieters; Caroline Demeyer, both of Laarne, Belgium

[73] Assignee: Exotic Plant, Laarne, Belgium

[21] Appl. No.: 770,494

[22] Filed: Dec. 20, 1996

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new cultivar of Vriesea named 'Condor' characterized by its upright branched dark purple inflorescence, and its medium green, glossy foliage with thin dark green transverse markings.

1 Drawing Sheet

The present invention relates to a new and distinct cultivar of Vriesea, a genus within the family bromeliaceae, hereinafter referred to by the cultivar name 'Condor'. The new cultivar is a hybrid resulting from a cross of parent plants identified below.

Vriesea comprise a genus of over 200 species of herbaceous evergreen perennials suitable for cultivation in the home or under glass. Vriesea are predominantly epiphytic and are native to the tropics. For the most part the species vary in diameter from 7 or 8 inches to 3 or 4 feet and have rosettes of glossy, smooth edged leaves which may be entirely green, variously marked or variegated.

Floral bracts of Vriesea frequently have brilliant colors and may last for many months. The range of bract colors for Vriesea is generally yellow, orange, red and red-purple. Tabular, three petalled flowers may also appear on the scape from under the colorful bracts, but are usually short lived.

Vrieseas may be advantageously grown as pot plants for greenhouse or home use. Desirably the plants are shaded from direct sunlight and the central vase-like part of the leaf rosette is normally filled with water.

Vriesea is native to tropical America. Leaves of the Vriesea are usually arranged in basal rosettes which are stiff and entire in several vertical ranks. Vriesea have terminal spikes which are bracted.

Asexual propagation of Vriesea is frequently done through the use of tissue culture practices. Propagation can also be from off-shoots produced by the plant which may then be rooted. The resulting plantlets are detached from the mother plant and may be potted up in a suitable growing mixture.

The new cultivar'Condor' is a product of a planned breeding program and was originated by the inventors Luc Pieters and Caroline DeMeyer from a cross made during such a program Laarne, Belgium Jan. 1, 1991. The male, or pollen parent, was a selection from *Vriesea succri* spec. *Pin.*. The female, or seed parent, was a selection from *Vriesea poelmanii* spec. *N* 3 *Pin.*. The selection comprising the new variety was chosen after commencement of flowering of the progeny in Laarne, Belgium Feb. 15, 1994. Subsequent asexual propagation by offshoots and tissue culture has demonstrated that the combination of characteristics as herein disclosed for the new cultivar 'Condor' are firmly fixed and are retained through successive generations of asexual reproduction.

Vriesea'Condor' is particularly characterized by its upright branched inflorescence with dark purple bracts, and by its glossy, foliage with thin dark green transverse markings.

Perhaps the closest comparison cultivar is *Vriesea poelmanii* 'Barbara' which is characterized by its red longlasting blooms, and medium green glossy foliage. 'Condor' has dark purple bracts, and dark green transverse markings on its foliage. 'Condor' has not been tested under all environmental conditions. The phenotype may vary with variations in environmental conditions such as temperature, light intensity, day length and humidity, without, however, any variation in genotype.

The accompanying color photographic drawing shows typical characteristics of 'Condor' with colors being as nearly true as possible with illustrations of this type. The photograph illustrates a typical 22 month old plant of 'Condor' grown from an offshoot, and finished in a 15.5 cm pot.

The following description is taken from the plant illustrated in the photograph. The plant was grown in Laarne, Belgium by the inventors under greenhouse conditions which are typical of the industry. Color references are made to The Royal Horticultural Society Colour Chart (R.H.S.).

Classification:

PLANT

A. General appearance:

*Form.*—Basal rosette growth habit, comprised of strap-like leaves arranged around a central axis.

*Height.*—Approximately 45–50 cm including inflorescence.

*Diameter.*—Approximately 52–58 cm.

B. Foliage:

*Color.*—The leaves are medium green with thin dark green transverse markings. The upper surface is darker and greener than, but closest to, 137 A with thin dark green markings of 139 A. The lower surface is 137 C with thin dark green markings of 137 A. The leaf base is often tinged with 165 C D.

*Size of leaf.*—The basal leaves are approximately 43 cm to 45 cm long, and 4.5 cm to 5.0 cm wide (flattened). At their widest point, near the base, the leaves are approximately 8.5 cm.

*Shape of leaf.*—The leaf blade is ligulate with an cuspidate tip. The margins are entire, and the leaves are curved over their length. The leaf is channeled, and the tip is notably twisted, wavy and curved downward.

*Surface texture.*—The leaf blade is thin, coriaceous, smooth and glossy.

*Average number of leaves.*—The plant produces approximately 29 leaves before producing an inflorescence.

Bracts

Dimensions and color: The floral bracts (with underlying sessile flowers or lateral branch spikes) are approximately 3.9 cm to 4.3 cm long, 3.9 cm to 4.3 cm wide (flattened), and more purple than, but closest to, 59 A, 187 D with translucent margins.

General shape: Individual bracts are broadly ovate, with an acute tip, and are folded at the center. The base of the bract encircles the scape. The tips of the bracts are curved inward toward the scape. The bracts are arranged imbricate, and alternate along the scape giving the inflorescence a flattened appearance. The bracts separate slightly from the scape as the flowers emerge.

Branch spikes: The inflorescence has approximately 6 branches, each of which is approximately 12 cm to 14 cm long, 3.9 cm to 4.4 wide, and contain approximately 12 flowers. Plants of 'Condor' often have offshoots emerging from the base which produce small unbranched inflorescences when the plant is chemically induced to flower. The scape bracts are approximately 6.9 cm to 10.5 cm long, and 3.0 cm to 3.4 cm wide, and resemble short leaves. The scape bracts are 146 CD, often streaked with purple 187 A.

Number: There are approximately 95 floral bracts in the entire inflorescence, and approximately 13 scape bracts.

Texture: Smooth and glossy.

Margin: Entire.

Scape: The scape is approximately 49 cm tall, 8 mm in diameter, and 145 C in color, lightly flushed with purple.

Flowers

Borne: Lateral, alternate from under floral bracts along the scape.

Shape of inflorescence: The inflorescence is a terminal branched spike with alternate, overlapping imbricate bracts, and approximately 6 branch spikes.

Individual flowers:

*Quantity.*—Approximately 95 flowers/buds present in terminal inflorescence, depending on the size of plant. Branch spikes are present, each containing approximately 14 flowers.

*Calyx.*—Sepals ovate. Three sepals present, approximately 2.9 cm long and 1.0 cm wide, and translucent 145 CD in color.

*Corolla.*—Petals ligulate, fused at the base around the ovary. There petals present, approximately 3.1 cm in long, and 5 mm wide translucent yellow 11 A at the petal tip, yellow 1 D throughout.

*Time of blooming.*—In mature plants, flowering begins approximately 16 weeks after induction, at any time of the year.

*Duration of blooms.*—The inflorescence will hold its color approximately 3 months; individual flowers last 1 day.

Floral Organs

Ovary: Superior, conical, three locules, approximately 4 mm in length.

Pistil: Approximately 3.3 cm long, 1 mm wide, 154 D in color. Stigmatic surface 2 mm wide, divided into three convoluted lobes, 154 D in color.

Stamens: Six present, filament 2.5 cm long, 0.8 mm wide. Anthers 5 mm long, yellow 7 BD in color.

Seed Characteristics

Typical for *Vriesea poelmanii* cultivars.

We claim:

1. A new and distinct cultivar of Vriesea plant named 'Condor', as illustrated and described.

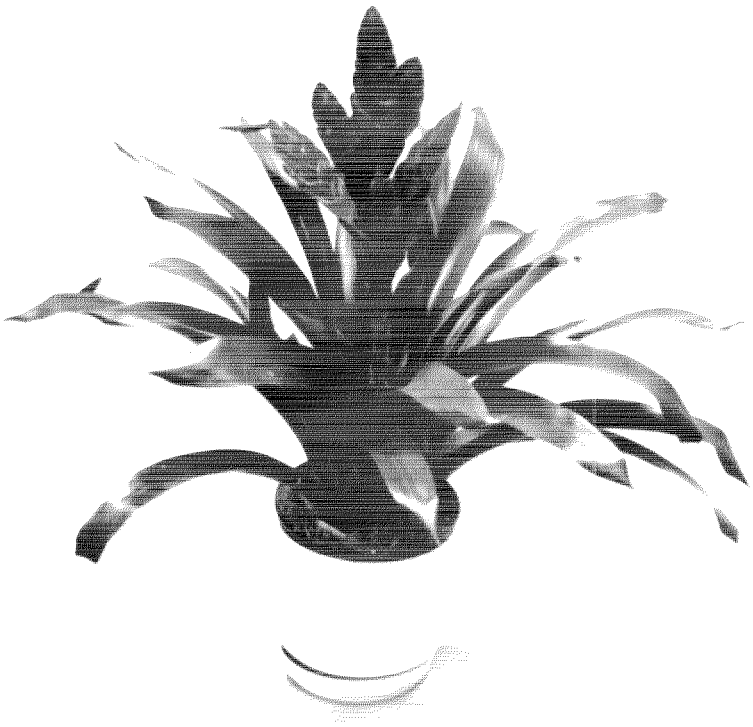

* * * * *